United States Patent
Kawashima

(10) Patent No.: US 9,018,435 B2
(45) Date of Patent: Apr. 28, 2015

(54) PAPER DIAPER

(76) Inventor: Kiyoharu Kawashima, Osaka (JP)

(*) Notice: Subject to any disclaimer, the term of this patent is extended or adjusted under 35 U.S.C. 154(b) by 429 days.

(21) Appl. No.: 13/398,334

(22) Filed: Feb. 16, 2012

(65) Prior Publication Data

US 2012/0215190 A1 Aug. 23, 2012

(30) Foreign Application Priority Data

Feb. 17, 2011 (JP) ................. 2011-032202

(51) Int. Cl.
- A61F 13/15 (2006.01)
- A61F 13/42 (2006.01)
- A61L 15/56 (2006.01)
- A61F 13/84 (2006.01)

(52) U.S. Cl.
CPC ......... *A61F 13/42* (2013.01); *A61F 2013/8497* (2013.01); *A61F 2013/422* (2013.01); *A61L 15/56* (2013.01)

(58) Field of Classification Search
CPC .............. A61F 13/42; A61F 2013/422; A61F 2013/8497
USPC ................................ 604/358, 613
See application file for complete search history.

(56) References Cited

U.S. PATENT DOCUMENTS

| | | | | |
|---|---|---|---|---|
| 5,130,290 A | * | 7/1992 | Tanimoto | 503/201 |
| 5,947,943 A | * | 9/1999 | Lee | 604/361 |
| 8,623,290 B2 | * | 1/2014 | Song et al. | 422/400 |
| 2009/0306612 A1 | * | 12/2009 | Husmark et al. | 604/360 |
| 2011/0144603 A1 | * | 6/2011 | Song | 604/361 |
| 2012/0172825 A1 | * | 7/2012 | Ales et al. | 604/361 |

FOREIGN PATENT DOCUMENTS

| JP | 59-088405 U | 6/1984 |
|---|---|---|
| JP | 2005-185643 A | 7/2005 |

* cited by examiner

*Primary Examiner* — Lynne Anderson
*Assistant Examiner* — Bradley Philips
(74) *Attorney, Agent, or Firm* — Osha Liang LLP

(57) ABSTRACT

Provided is a paper diaper which is safe to a wearer thereof and also has additional values of, for example, developing a plurality of colors and providing a practical effect of instantaneously detecting that the wearer has urinated, or the like. In a paper diaper 11 including a back sheet 13 for covering an outer side of an absorption body 14 for absorbing urine, an indicator portion 15 containing a colorless color-developing agent formed of an electron-donating coloration compound is formed by application on a wide range of an inner surface of the back sheet 13, and a color development assisting agent 16 is provided on the indicator portion 15. The color development assisting agent 16 is dissolved in the urine to contact the indicator portion 15, thus to cause the indication portion 15 to develop a color.

8 Claims, 8 Drawing Sheets

PAPER DIAPER

BACKGROUND OF THE INVENTION

1. Field of the Invention

The present invention relates to a paper diaper including an indicator, and more specifically to a paper diaper providing both safety and practicality.

2. Description of the Prior Art

There is an indicator of a paper diaper, the color of which is changed from one color to another color (see, for example, Patent Document 1).

Such an indicator has the following structure. On an inner side of a back sheet of the paper diaper, a color layer formed of water-insoluble blue ink is provided; and on the color layer, a color change layer formed of water-soluble yellow ink is provided. Before being wetted with urine, the indicator appears green as a result of the blue color of the color layer and the yellow color of the color change layer being combined. However, when the indicator is wetted with urine, the yellow ink of the color change layer is dissolved, and the color of the color change layer is faded. As a result, the indicator appears blue as a whole. The indicator indicates that the wearer of the paper diaper has urinated by this color change from green to blue. The yellow ink which has dissolved in urine is absorbed to an absorption body covered with the back sheet.

However, all the yellow ink is not quickly absorbed to the absorption body, and thus a peripheral portion of the indicator appears to be blotted with the yellow ink and the external appearance of the paper diaper is unpleasant. For this reason, the indicator is conventionally formed to be shaped as one thin line.

With such an indicator formed of one thin line, especially when the amount of urine is small or when the position of urination is shifted from the position of the indicator, it may not be clearly determined that the color has changed. Since the indicator is narrow, the amount of urine is not easily estimated from the color change of the indicator. In such a case, the paper diaper is unnecessarily replaced.

Patent Document 2 proposes an indicator which uses color-developing ink, instead of the indicator, the color of which is changed. The color-developing ink is formed of a combination of an ink binder, a colorant, a pH adjusting agent, solvent-containing ink, and a developer. The colorant, which is colorless owing to the function of the pH adjusting agent, is colored by the function of the developer which is formed of a basic substance. The indicator formed of such ink has a hue thereof changed by cleavage of a lactone ring of the developer and thus does not provide an unpleasant external appearance due to the indicator being blotted.

Examples of usable basic substances include ammonia, sodium bicarbonate, calcium carbonate, magnesium carbonate, magnesium aluminosilicate, magnesium oxide, calcium oxide, calcium hydroxide, magnesium hydroxide, calcium silicate, magnesium silicate and the like. Much care is needed in selecting a basic substance so that there is no harm to infants, who are delicate. A basic substance merely has a function of changing the color, and one basic substance cannot develop a plurality of colors. In addition, the indicator is not colored instantaneously, but requires several minutes to be colored.

PRIOR ART DOCUMENT

Patent Document

Patent Document 1: Japanese Laid-Open Utility Model Publication No. 59-88405
Patent Document 2: Japanese Laid-Open Patent Publication No. 2005-185643

SUMMARY OF THE INVENTION

Problems to be Solved by the Invention

The present invention has an object of providing a paper diaper which is safe to a wearer thereof and also has additional values of, for example, developing a plurality of colors and providing a practical effect of instantaneously detecting that the wearer has urinated or the like.

Means for Solving the Invention

The means for achieving the object is a paper diaper including a back sheet for covering an outer side of an absorption body for absorbing urine. The paper diaper includes an indicator portion containing a colorless color-developing agent formed of an electron-donating coloration compound, the indicator portion being provided on the back sheet; and a color development assisting agent which is activated by water contained in the urine having a temperature of 36° C.±2° C. to contact the indicator portion, thus to cause the indication portion to develop a color, the color development assisting agent being provided in the vicinity of the indicator portion.

The expression "the indicator portion is provided on the back sheet" means that the indicator is directly formed on the back sheet, that the indicator is separately formed and secured to the back sheet, or that the indicator is held in a state of being along the back sheet.

When the color development assisting agent is wetted with urine, the color development assisting agent is dissolved in water contained in the urine having a temperature close to the body temperature and thus contacts the indicator portion. As a result, the indicator, which has been colorless, is colored. In other words, the color development assisting agent is activated by the water contained in the urine to cause the indicator portion to develop a color. Since the indicator portion is colored from a colorless state, it can be clearly determined whether or not the wearer of the paper diaper has urinated.

The indicator portion may be formed by application or printing performed on a surface of the back sheet, the surface facing the absorption body. In the case where the back sheet allows a small amount of water to permeate therethrough, the indicator portion may be formed on a surface of the back sheet opposite to the surface facing the absorption body, by application or printing. Alternatively, the indicator portion may be formed on a separate sheet material, and the sheet material may be attached to the back sheet. In the former case, the indicator is visually recognizable directly, instead of being seen through the back sheet, and thus the color development state can be checked clearly.

The color development assisting agent may be dried after being applied to, printed on, or immersed in, a sheet material, and the sheet material may be provided between the indicator portion and the absorption body. Alternatively, the color development assisting agent may be applied or printed adjacent to the indicator portion.

The color development assisting agent may be in a powder form and may be mixed in the absorption body. In the case where the color development assisting agent is in a liquid state, the liquid color development assisting agent may be immersed in the absorption body and then dried. Since no separate member is required for providing the color development assisting agent, the paper diaper can be produced easily and at low cost.

The color-developing agent may contain at least one of rhodamine B lactam, 6-diethylamino-benzo[a]fluoran, 3-diethylamino-benzo[a]fluoran, 3-diethylamino-7,8-benzo[a]fluoran, 9-diethylamino-benzo[a]fluoran, 3-diethylamino-7-chlorofluoran, 3,3-bis(1-n-butyl-2-methyl-indoyl-3)phthalate, 3,3-bis(1-ethyl-2-methyl-indoyl-3)phthalate, 3,6-bis(diethylamino)fluoran-γ-(4'-nitro) anilinolactam, 3-diethylamino-6-methyl-7-chlorofluoran, 2-bromine-3-methyl-6-dibutylaminofluoran, 1,3-dimethyl-6-diethylaminofluoran, 1,3,3-trimethyl-indolino-7'-chloro-β-naphthospiropyran, 3-cyclohexylamino-6-chlorofluoran, 2-(phenyliminoethanezyliden)-3,3-trimethylindoline, N-acetylauramine, N-phenylauramine, 2-{2-[4-(dodecyloxy)-3-methoxyphenyl]-ethenyl}quinoline, marachite green lactone, 3-diethylamino-7-dibenzoylaminofluoran, 3-diethylamino-7-chloroanilinofluoran, 3,6,5'-tri(diethylamino)fluorene-9-spiro-1'-(3'-isobenzofuran), 2,N,N-dibenzylamino-6-diethylaminofluoran, 3-(N,N-diethylamino)-7-(N,N-dibenzylamino)fluoran, 3-[2,2-bis(1-ethyl-2-methylindoyl-3)vinyl]-3-(4-diethylaminophenyl)-phthalide, 3,3-bis(4-diethylamino-2-ethoxyphenyl)-4-azaphthalide, crystal violet lactone, ethyl leuco methylene blue, methoxybenzoyl leuco methylene blue, di-β-naphthospiropyran, 3,3-bis(4-diethylaminophenyl)-6-diethylaminophthalide, 3-(4-diethylamino-2-ethoxyphenyl)-3-(1-ethyl-2-methylindoyl-3)-4-azaphthalide, 3-(4-diethylaminophenyl)-3-(1-ethyl-2-methylindoyl-3)-phthalide, 3-cyclohexylmethylamino-6-methyl-7-anilinofluoran, 3-diethylamino-6-methyl-7-anilinofluoran, 3-n-dibutylamino-6-methyl-7-anilinofluoran, 3-diethylamino-6-methyl-7-kylindenofluoran, 2-(2-chloroanilino)-6-diethylaminofluoran, 2-(2-chloroanilino)-6-dibutylaminofluoran, 2-anilino-3-methyl-6-diethyllaminofluoran, 2-anilino-3-methyl-6-dibutylaminofluoran, 6-diethylamino-3-methyl-2-(3-toluideno)-fluoran, 6-diethylamino-3-methyl-2-(2,4-kylindeno)-fluoran, 6-diethylamino-3-methyl-2-(2,6-kylindeno)-fluoran, trade name "S20" produced by Yamamoto Chemicals Inc., trade name "Red 8" produced by Yamamoto Chemicals Inc., trade name "Red 49" produced by Yamamoto Chemicals Inc., trade name "Red 520" produced by Yamada Chemical Co., Ltd., trade name "Red 100" produced by Hodogaya Chemical Co., Ltd., trade name "NC-Red-4" produced by Hodogaya Chemical Co., Ltd., trade name "NC-Red-6" produced by Hodogaya Chemical Co., Ltd., trade name "PSD-HP" produced by Nippon Soda Co., Ltd., trade name "Orange 100" produced by Yamada. Chemical Co., Ltd., trade name "Leuco Yellow" produced by Leuco, trade name "Green 300" produced by Yamada Chemical Co., Ltd., trade name "YK-ATP" produced by Yamamoto Chemicals Inc., trade name "Green 300" produced by Hodogaya Chemical Co., Ltd., trade name "Blue 200" produced by Hodogaya Chemical Co., Ltd., trade name "CVL. sp" produced by Hodogaya Chemical Co., Ltd., trade name "S205" produced by Yamada Chemical Co., Ltd., and trade name "Black 100" produced by Yamada Chemical Co., Ltd. Owing to this, at least red, orange, yellow, green, blue and black, also a mixed color thereof, for example, purple can be developed.

The color development assisting agent may contain at least one of polyphenol, catechin, tannin, gallnut, gallic acid, propyl gallate, persimmon tannin, green tea catechin (green tea tannin), green tea polyphenol, apple tannin, grape tannin, perilla tannin, perilla seed tannin, cacao tannin, cacao polyphenol, ascorbic acid, thiamine hydrochloride, adipic acid, citric acid, glycolic acid, succinic acid, tartaric acid, sebasic acid, sorbic acid, lactic acid, fumaric acid, and malic acid. The "polyphenol" refers to flavonoid such as catechin, tannin or the like which are called by various names, or phenoric acid. All of the above-listed substances are harmless to the human body. Polyphenol, especially, has a deodorizing effect or the like. When any of the above-listed substances is used, a plurality of colors can be developed with a single color development assisting agent.

The indicator portion may contain a surfactant. In this case, the color development can be caused more quickly.

The indicator portion may be provided in the entirety of a part of the back sheet which is in contact with the absorption body. In this case, a reaction occurs even when the amount of urine is small or even when the position of urination is shifted from the position of the indicator. Moreover, the amount of urine is easily estimated from an external appearance.

The indicator portion may be formed of at least one of a graphic pattern, a designed pattern, and a letter. The graphic pattern or the like appearing at the time of color development amuses the wearer or the care-take.

Effect of the Invention

According to the present invention, a change from a colorless state to a colored state informs that the wearer of the paper diaper has urinated. Thus, it is easily determined that the wearer has urinated by an external appearance thereof. Moreover, as a color development assisting agent for causing a coloration reaction, a substance which can quickly cause a coloration reaction at a temperature of the urine at the time of excretion and is harmless to the human body is usable. Therefore, the safety for the wearer is obtained easily. In the case where the color development assisting agent is a substance having a deodorizing function such as polyphenol or the like, deodorization of urine or the like is expected. Moreover, a multi-color indicator can be provided with a single color development assisting agent, and also the indicator can be colored instantaneously when the wearer urinates. Thus, a highly practical paper diaper is provided.

DESCRIPTION OF THE PREFERRED EMBODIMENTS

One embodiment of the present invention will be described with reference to the drawings.

Figure 1:
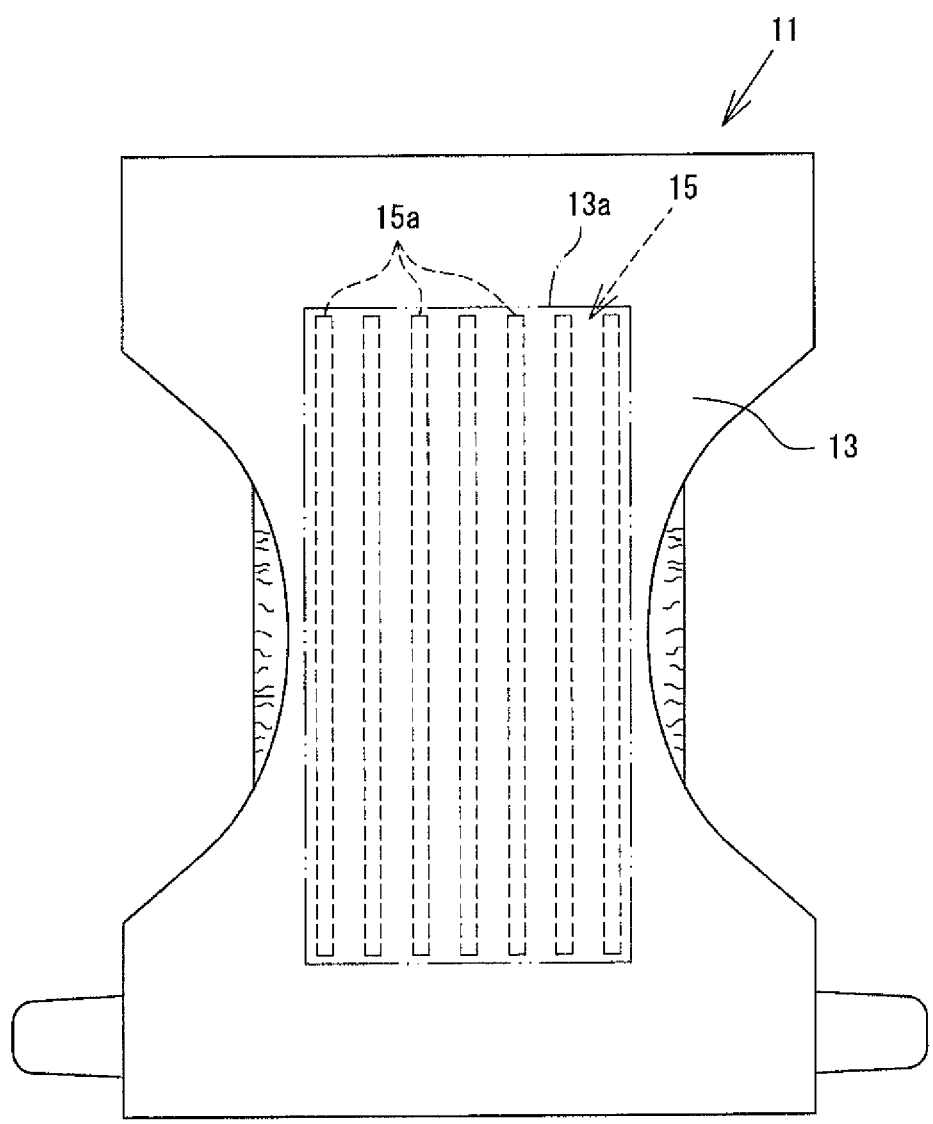
FIG. 1 is a schematic plan view showing an outer surface of a paper diaper.
Figure 2:
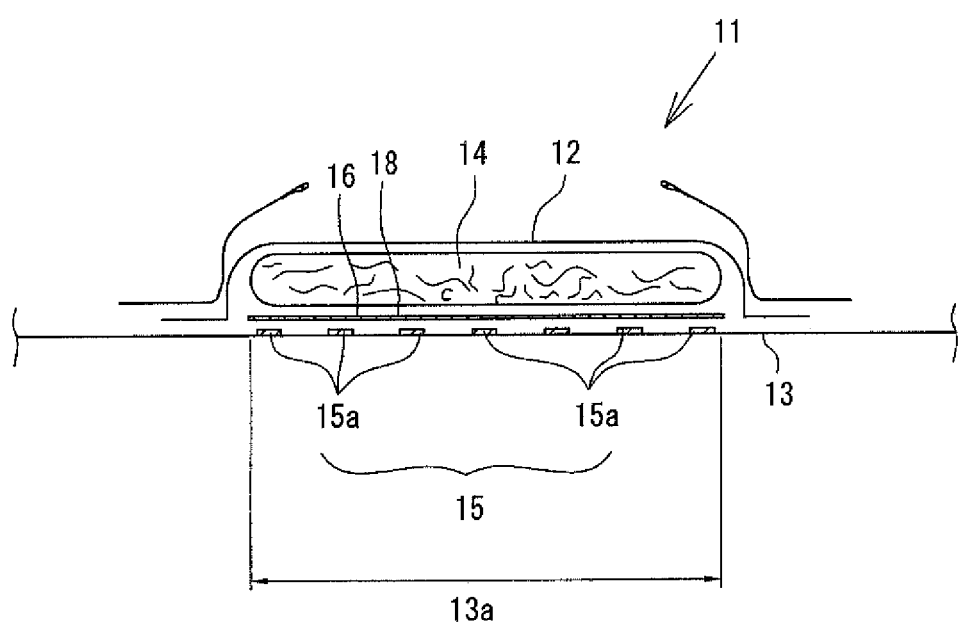
FIG. 2 is a schematic view showing a cross-sectional structure of the paper diaper.

FIG. 1 is a developed view showing an outer surface of a paper diaper 11, and FIG. 2 is a schematic structural view showing a cross-sectional structure thereof.

As shown in these figures, the paper diaper 11 includes an absorption body 14 provided between a water-permeable top sheet 12 and a water-non-permeable back sheet 13. Namely, an outer surface of the absorption body 14 for absorbing urine (water) is covered with the back sheet 13. The back sheet 13 is light-transmissive. The back sheet 13 has a great number of minute holes which do not allow water molecules to pass therethrough but allow vapor to pass therethrough so that a wearer of the paper diaper 11 does not become sweaty.

An indicator portion 15 is provided on the back sheet 13. In the vicinity of the indicator portion 15, a color development assisting agent 16 is provided.

The indicator portion 15 contains a colorless color-developing agent formed of an electron-donating coloration compound. The color development assisting agent is dissolved in a liquid which is to be absorbed to the absorption body 14, namely, urine, more specifically, urine having a temperature of about 36° C. and contacts the indicator portion 15. As a result, the indicator portion 15 is colored.

The indicator portion 15 is formed by applying ink containing the color-developing agent to a surface of the back sheet 13 facing the absorption body 14 by appropriate means. The indicator portion 15 is formed in the entirety of an absorption body area 13a, which is a part of the back sheet 13 that is in direct or indirect contact with the absorption body 14.

In the example of FIG. 1, the absorption body area 13a has a rectangular shape which is longer in a longitudinal direction, and the indicator portion 15 provided in the absorption body area 13a includes a plurality of linear indicator carriers 15a arrayed parallel to each other with a gap therebetween. The width, the size of the gap and the number of the indicator carriers 15a are appropriately set.

Since the ink used to form the indicator portion 15 is colorless, the indicator portion 15 is not visible. Thus, the indicator portion 15 is represented with dashed lines for the sake of convenience in, for example, FIG. 1. The ink is obtained by mixing the color-developing agent of any of various colors, a solvent, and a surfactant. In the case of the indicator portion 15 including the plurality of indicator carriers 15a, it is preferable that the color-developing agents for different colors are used for the plurality of linear indicator carriers 15a, because the indicator portion 15 is made colorful in this manner.

Figure 3:
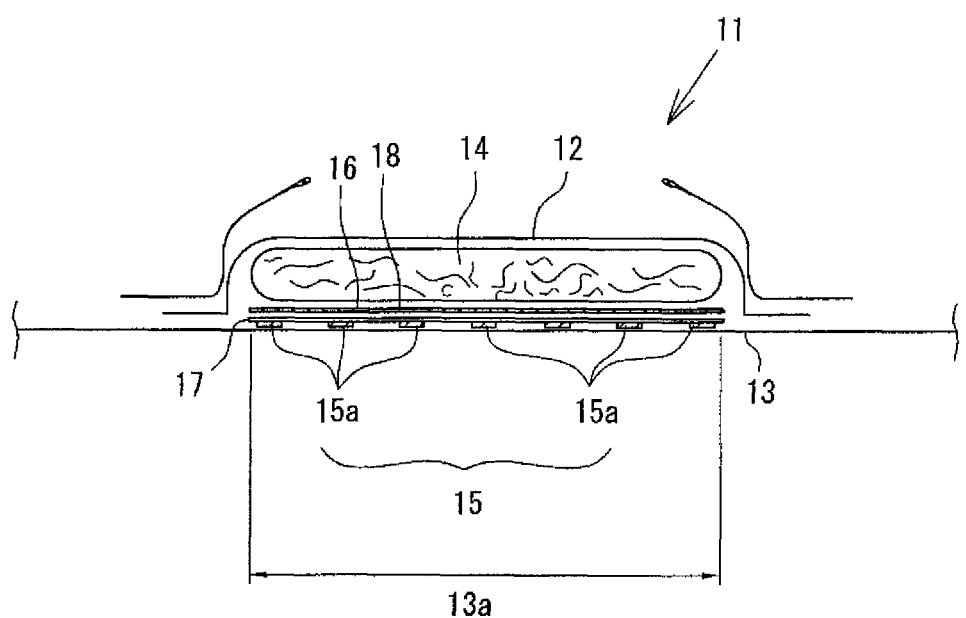
FIG. 3 is a schematic view showing another cross-sectional structure of a paper diaper.

Instead of being formed by directly applying the ink to the back sheet 13, the indicator portion 15 may also be formed as shown in FIG. 3, for example. Specifically, the ink is applied to an appropriate water-absorptive sheet material 17, and the sheet material 17 is attached to the back sheet 13. A surface of the sheet material 17 on which the ink has been applied (indicator portion 15 forming surface) is attached to the surface of the back sheet 13 facing the absorption body 14. The sheet material 17 may be bonded to the back sheet 13, secured to the absorption body 14, or indirectly held by securing the absorption body 14.

The color development assisting agent 16 is incorporated into the paper diaper 11 so as to make a set together with the indicator portion 15. The color development assisting agent 16 does not need to be in close contact with the indicator portion 15, but it is preferable that the color development assisting agent 16 is as proximate as possible to the indicator portion 15 in order to react to urination quickly.

In the example of FIG. 2, the color development assisting agent 16 is applied to (immersed in) a sheet material 18, and the sheet material 18 is provided between the indicator portion 15 and the absorption body 14 (see FIG. 2). Specifically, the color development assisting agent 16 is put into a liquid state by a solvent, immersed in the sheet material 18 formed of an appropriate material such as crepe paper or the like, and then dried. Thus, the color development assisting agent 16 is formed into a color development assisting agent sheet.

Figure 4:
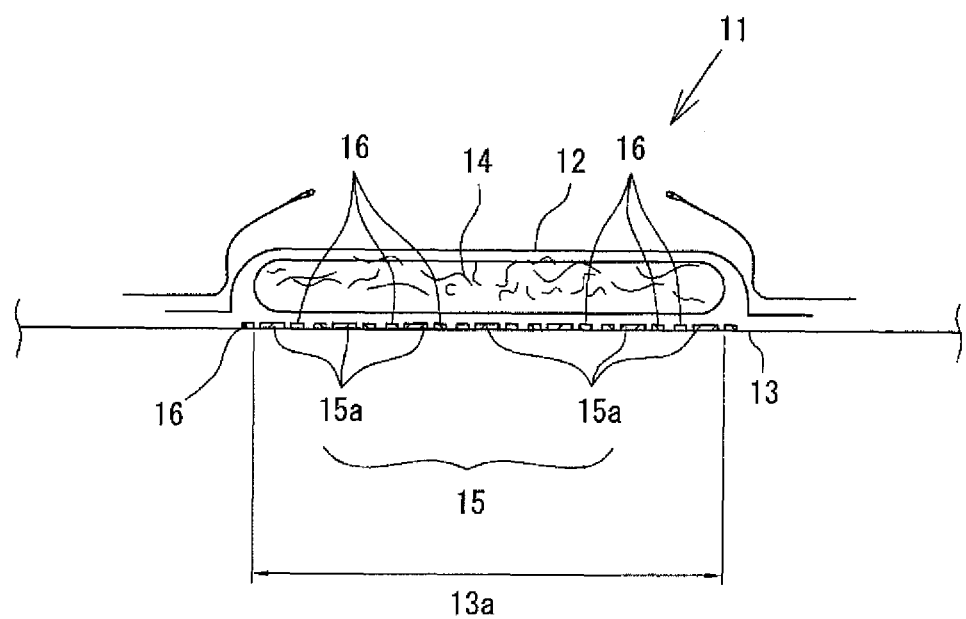
FIG. 4 is a schematic view showing still another cross-sectional structure of a paper diaper.

As shown in FIG. 4, the color development assisting agent 16 may be applied to the back sheet 13 adjacently to the indicator portion 15 (indicator carriers 15a).

Figure 5:
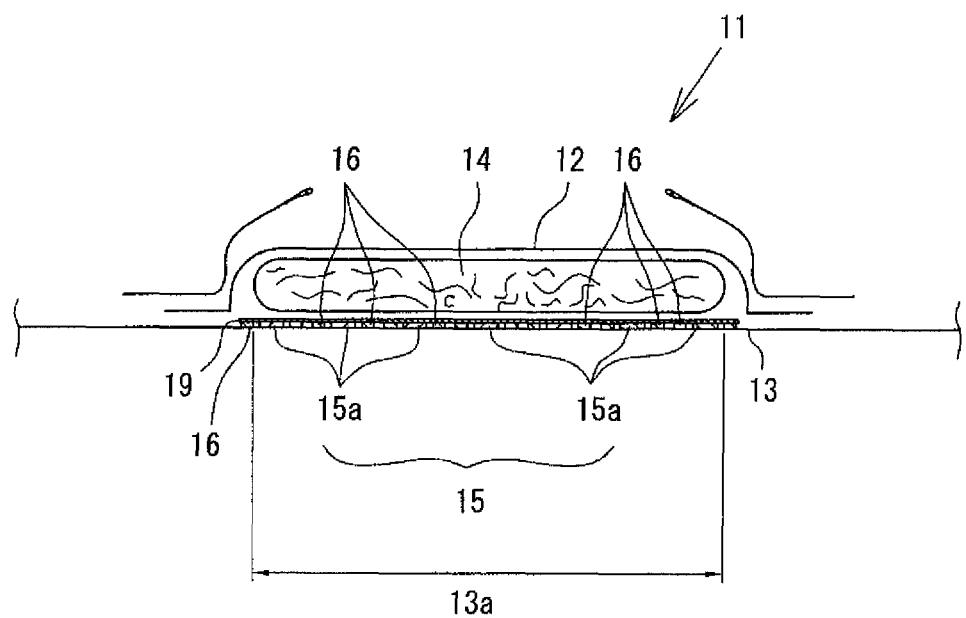
FIG. 5 is a schematic view showing still another cross-sectional structure of a paper diaper.

As shown in FIG. 5, the indicator portion 15 and the color development assisting agent 16 may be applied to an appropriate sheet material 19 at adjacent areas to each other, and the indicator portion 15 part of the sheet material 19 may be attached to, and held by, the back sheet 13. In the example of FIG. 5, the color development assisting agent 16 is applied to the same surface as the indicator portion 15, but may be applied to an opposite surface to the indicator portion 15.

Although not shown, the absorption body 14 impregnated with the color development assisting agent 16 and dried may be provided as an absorption body containing the color development assisting agent. Alternatively, the color development assisting agent 16 in a powder form may be mixed in, and held by, the absorption body 14.

As described above, the back sheet 13 has a great number of minute holes so that the wearer of the paper diaper 11 does not become sweaty. In the case where only ethanol and IPA are used as the solvents of the ink, the minute holes in the back sheet 13 are expanded, and as a result, the ink applied to the surface of the back sheet 13 facing the abruption body 14 permeates into an outer surface of the back sheet 13. When this occurs, a small number of water molecules also pass to the outer surface of the back sheet 13.

By contrast, in the case where ethanol, IPA and either ethyl acetate or methyl acetate are used as the solvents of the ink, the minute holes of the back sheet 13 do not expand and ink does not permeate.

The back sheet 13 has the above-described property. Therefore, in the case where only ethanol and IPA are used as the solvents of the ink, the indicator portion 15 may be formed on the outer surface of the back sheet 13 although not shown.

Examples of substances usable as the color-developing agent include the following substances.

Substances which develop red are shown in Table 1.

TABLE 1

| No. | Developing red |
|---|---|
| 1 | Rhodamine B lactam |
| 2 | 6-diethylamino-benzo[a]fluoran |
| 3 | 3-diethylamino-benzo[a]fluoran |
| 4 | 3-diethylamino-7,8-benzofluoran |
| 5 | 9-diethylamino-benzo[a]fluoran |
| 6 | 3-diethylamino-7-chlorofluoran |
| 7 | 3,3-bis(1-n-butyl-2-methyl-indoyl-3)phthalate |
| 8 | 3,3-bis(1-ethyl-2-methyl-indoyl-3)phthalate |
| 9 | 3,6-bis(diethylamino)fluoran-γ-(4'-nitro)anilinolactam |
| 10 | 3-diethylamino-6-methyl-7-chlorofluoran |
| 11 | 2-bromine-3-methyl-6-dibutylaminofluoran |

Substances which develop orange are shown in Table 2.

TABLE 2

| No. | Developing orange |
|---|---|
| 12 | 1,3-dimethy-6-diethylaminofluoran |
| 13 | 1,3,3-trimethy-indolino-7'-chloro-β-naphthospiropyran |
| 14 | 3-cyclohexylamino-6-chlorofluoran |

Substances which develop yellow are shown in Table 3.

TABLE 3

| No. | Developing yellow |
|---|---|
| 15 | 2-(phenyliminoethanezyliden)-3,3-trimethylindoline |
| 16 | N-acetylauramine |
| 17 | N-phenylauramine |
| 18 | 2-[2-[4-(dodecyloxy)-3-methoxyphenyl]-ethenyl}quinoline |

Substances which develop green are shown in Table 4.

TABLE 4

| No. | Developing green |
|---|---|
| 19 | Marachite green lactone |
| 20 | 3-diethylamino-7-dibenzoylaminofluoran |
| 21 | 3-diethylamino-7-chloroanilinofluoran |
| 22 | 3,6,5'-tri(diethylamino)fluorene-9-spiro-1'-(3'-isobenzofuran) |
| 23 | 2,N,N-dibenzylamino-6-diethylaminofluoran |
| 24 | 3-(N,N-diethylamino)-7-(N,N-dibenzylamino)fluoran |
| 25 | 3-[2,2-bis(1-ethyl-2-methylindoyl-3)vinyl]-3-(4-diethylaminophenyl)-phthalide |
| 26 | 3,3-bis(4-diethylamino-2-ethoxyphenyl)-4-azaphthalide |

Substances which develop blue are shown in Table 5.

TABLE 5

| No. | Developing blue |
|---|---|
| 27 | Crystal violet lactone |
| 28 | Ethyl leuco methylene blue |
| 29 | Methoxybenzoyl leuco methylene blue |
| 30 | Di-β-naphthospiropyran |
| 31 | 3,3-bis(4-diethylaminophenyl)-6-diethylaminophthalide |
| 32 | 3-(4-diethylamino-2-ethoxyphenyl)-3-(1-ethyl-2-methylindoyl-3)-4-azaphthalide |
| 33 | 3-(4-diethylaminophenyl)-3-(1-ethyl-2-methylindoyl-3)-phthalide |

Substances which develop black are shown in Table 6.

TABLE 6

| No. | Developing black |
|---|---|
| 34 | 3-cyclohexylmethylamino-6-methyl-7-anilinofluoran |
| 35 | 3-diethylamino-6-methyl-7-anilinofluoran |
| 36 | 3-n-dibutylamino-6-methyl-7-anilinofluoran |
| 37 | 3-diethylamino-6-methyl-7-kylindenofluoran |
| 38 | 2-(2-chloroanilino)-6-diethylaminofluoran |
| 39 | 2-(2-chloroanilino)-6-dibutylaminofluoran |
| 40 | 2-anilino-3-methyl-6-diethylaminofluoran |
| 41 | 2-anilino-3-methyl-6-dibutylaminofluoran |
| 42 | 6-diethylamino-3-methyl-2-(3-toluideno)-fluoran |
| 43 | 6-diethylamino-3-methyl-2-(2,4-kylindeno)-fluoran |
| 44 | 6-diethylamino-3-methyl-2-(2,6-kylindeno)-fluoran |

Among the substances which develop red, substances specified by trade names are shown in Table 7.

TABLE 7

| No. | Developing red |
|---|---|
| 45 | Trade name "S20" produced by Yamamoto Chemicals Inc. |
| 46 | Trade name "Red 8" produced by Yamamoto Chemicals Inc. |
| 47 | Trade name "Red 49" produced by Yamamoto Chemicals Inc. |
| 48 | Trade name "Red 520" produced by Yamada Chemical Co., Ltd. |
| 49 | Trade name "Red 100" produced by Hodogaya Chemical Co., Ltd. |
| 50 | Trade name "NC-Red-4" produced by Hodogaya Chemical Co., Ltd. |
| 51 | Trade name "NC-Red-6" produced by Hodogaya Chemical Co., Ltd. |
| 52 | Trade name "PSD-HP" produced by Nippon Soda Co., Ltd. |

Among the substances which develop orange, a substance specified by a trade name is shown in Table 8.

TABLE 8

| No. | Developing orange |
|---|---|
| 53 | Trade name "Orange 100" produced by Yamada Chemical Co., Ltd. |

Among the substances which develop yellow, a substance specified by a trade name is shown in Table 9.

TABLE 9

| No. | Developing yellow |
|---|---|
| 54 | Trade name "Leuco Yellow" produced by Leuco |

Among the substances which develop green, substances specified by trade names are shown in Table 10.

TABLE 10

| No. | Developing green |
|---|---|
| 55 | Trade name "Green 300" produced by Yamada Chemical Co., Ltd. |
| 56 | Trade name "YK-ATP" produced by Yamamoto Chemicals Inc. |
| 57 | Trade name "Green 300" produced by Hodogaya Chemical Co., Ltd. |

Among the substances which develop blue, substances specified by trade names are shown in Table 11.

TABLE 11

| No. | Developing blue |
|---|---|
| 58 | Trade name "Blue 200" produced by Hodogaya Chemical Co., Ltd. |
| 59 | Trade name "CVL. sp" produced by Hodogaya Chemical Co., Ltd. |

Among the substances which develop black, substances specified by trade names are shown in Table 12.

TABLE 12

| No. | Developing black |
|---|---|
| 60 | Trade name "S205" produced by Yamada Chemical Co., Ltd. |
| 61 | Trade name "Black 100" produced by Yamada Chemical Co., Ltd. |

Examples of substances usable as the solvent include, for example, ethanol, methanol, IPA, ethyl acetate, methyl acetate, isopropyl acetate, normal propyne acetate, normal butyl acetate, cellosolve acetate, isobutyl acetate, DMF (dimethylformamide), acetone, MEK (methylethylketone), toluene, xylene, normal propanol, isobutanol, methyl cellosolve, ethyl cellosolve, normal butanol, cyclohexane, butyl cellosolve, MIBK (methylisobutylketone) and the like. These substances may be used independently or as a combination of a plurality thereof.

From the viewpoint of safety, it is preferable to use ethanol, IPA, DMF, ethyl acetate or methyl acetate.

Examples of substances usable as the surfactant include anionic, cationic, nonionic or amphoteric surfactants. It is desirable to use a nonionic surfactant, which is not liable to be influenced by an electron-donating coloration compound, a color development assisting agent or the like.

Examples of the nonionic surfactants are shown in Table 13.

TABLE 13

| No. | Nonionic surfactant |
|---|---|
| 1 | Polyoxyethylenenonylphenylether |
| 2 | Polyoxyethylenedistyrenated phenylether |
| 3 | Polyoxyethylenelaurylether |
| 4 | Polyoxyethyleneoleylether |
| 5 | Polyoxyethylene higher alcohol ether |
| 6 | Sorbitantrioleate |
| 7 | Polyoxyethylenesorbitanmonooleate |
| 8 | Polyoxyethylenepolyoxypropyleneglycol |
| 9 | Sorbitan sequisoleate |
| 10 | Sucrose fatty acid ester |

As the color development assisting agent, any of substances shown in Table 14 is usable from the viewpoint of safety.

TABLE 14

| No. | Color development assisting agent |
|---|---|
| 1 | Tannic acid |
| 2 | Gallic acid |
| 3 | Propyl gallate |
| 4 | Ascorbic acid |
| 5 | Thiamine hydrochloride |
| 6 | Adipic acid |
| 7 | Citric acid |
| 8 | Glycolic acid |
| 9 | Succinic acid |
| 10 | Tartaric acid |
| 11 | Sebasic acid |
| 12 | Sorbic acid |
| 13 | Lactic acid |
| 14 | Fumaric acid |
| 15 | Malic acid |

In order to check the effects of paper diapers having the above-described structure, the following types of indicator test ink (see Table 15) and the following types of color development assisting agent test ink (see Table 16) were prepared and experiments (experiments 1 through 9) were conducted.

TABLE 15

Composition of indicator test ink

| | | Type A | | | | | Type B | | | | | Type C | | | | |
|---|---|---|---|---|---|---|---|---|---|---|---|---|---|---|---|---|
| | | A red | A orange | A green | A blue | A black | B red | B orange | B green | B blue | B black | C red | C orange | C green | C blue | C black |
| Ethyl acetate | | | | | | | 25 | 25 | 25 | 25 | 25 | 25 | 25 | 25 | 25 | 25 |
| Ethanol | | 28 | 28 | 28 | 28 | 28 | | | | | | | | | | |
| IPA | | 50 | 50 | 50 | 50 | 50 | 53 | 53 | 53 | 53 | 53 | 50 | 50 | 50 | 50 | 50 |
| DMF | | 20 | 20 | 20 | 20 | 20 | 20 | 20 | 20 | 20 | 20 | 20 | 20 | 20 | 20 | 20 |
| Color-developing agent Numeral in < > represents the type of color-developing agent | Red <2> | 2 | | | | | 2 | | | | | 2 | | | | |
| | Orange <12> | | 2 | | | | | 2 | | | | | 2 | | | |
| | Green <26> | | | 2 | | | | | 2 | | | | | 2 | | |
| | Blue <31> | | | | 2 | | | | | 2 | | | | | 2 | |
| | Black <34> | | | | | 2 | | | | | 2 | | | | | 2 |
| Surfactant | | 0 | 0 | 0 | 0 | 0 | 0 | 0 | 0 | 0 | 0 | 3 | 3 | 3 | 3 | 3 |

*1. A: ink permeates to the other side; B and C: ink does not permeate to the other side.

TABLE 16

Composition of color development assisting agent ink

| | Type D | Type E |
|---|---|---|
| Ethanol and IPA | 90 | 90 |
| Color development assisting agent <3> | 7 | 10 |
| Surfactant | 3 | 0 |

*For type D, 10 types of ink were prepared by use of surfactants <1>-<10>.

As the indicator test ink used to form the indicator portion described above, type A which permeates to the rear side (outer surface) of the back sheet 13 from the surface facing the absorption body 14, and types B and C which do not permeate to the rear side of the back sheet 13 were prepared. Types A and B do not contain a surfactant, whereas type C contains a surfactant.

The indicator test ink of type A contains, as solvents, 28 parts by weight of ethanol, 50 parts by weight of IPA, and 20 parts by weight of DMF. As remaining 2 parts by weight, a color-developing agent is contained.

The indicator test ink of type B contains 25 parts by weight of ethyl acetate, 53 parts by weight of IPA, 20 parts by weight of DMF, and remaining 2 parts by weight of color-developing agent.

The indicator test ink of type C contains 25 parts by weight of ethyl acetate, 50 parts by weight of IPA, 20 parts by weight of DMF, 3 parts by weight of surfactant, and remaining 2 parts by weight of color-developing agent.

For forming the indicator test ink of each of types A, B and C, five types of ink respectively containing red, orange, green, blue and black color-developing agents were prepared. As the color-developing agent for red, "6-diethylamino-benzo[a]fluoran" (2nd; see Table 1) was used. As the color-developing agent for orange, "1,3-dimethyl-6-diethylaminofluoran" (12th; see Table 2) was used. As the color-developing agent for green, "3,3-bis(4-diethylamino-2-ethoxyphenyl)-4-azaphthalide" (26th; see Table 4) was used. As the color-developing agent for blue, "3,3-bis(4-diethylaminophenyl)-6-diethylaminophthalide" (31st; see Table 5) was used. As the color-developing agent for black, "3-cyclohexylmethylamino-6-methyl-7-anilinofluoran" (34th; see Table 6) was used.

As the color development assisting agent test ink used to form the color development assisting agent, type D containing a surfactant and type E not containing a surfactant were prepared.

The color development assisting agent test ink of type D contains 90 parts of weight of ethanol and IPA, 7 parts by weight of color development assisting agent, and 3 parts by weight of surfactant. The above-mentioned ten types of surfactants were used to prepare ten types of color development assisting agent test ink.

The color development assisting agent test ink of type E contains 90 parts of weight of ethanol and IPA and 10 parts by weight of color development assisting agent.

For forming the color development assisting agent test ink of both of types D and E, "propyl gallate", which is one type of polyphenol, was used as the color development assisting agent (3rd in the color development assisting agent list).

Experiment 1

Experiment 1 was conducted in order to check the significance of a surfactant. The indicator test ink of type A was applied to a back sheet to form an indicator portion. The indicator test ink of type B was applied to a back sheet to form an indicator portion. The color development assisting agent test ink of type E was applied to crepe paper and dried to form a color development assisting agent test paper sheet. The color development assisting agent test paper sheet was put on each of the above-formed indicator portions, and water of 36° C. was dropped thereto. It was determined whether or not a vivid color appeared immediately.

The results are as shown in Table 17. In the table, "quick" means that sufficient color development occurred within several seconds. "Good" means that sufficient color development occurred within 1 minute. "Slow" means that it took several minutes or more (generally 4 to 5 minutes) to cause color development. The degree of color development was determined by a visual check. "Dark" means that sufficient color development clearly occurred. "Good" means that necessary color development occurred. "Pale" means that the color development state was inferior to "good" but the occurrence of color development was confirmed. "Very pale" means sufficient color development did not occur. These criteria of evaluation are the same for the following experiments.

TABLE 17

| | Indicator test ink | | | | | | | | | |
|---|---|---|---|---|---|---|---|---|---|---|
| | Type A | | | | | Type B | | | | |
| | Red | Orange | Green | Blue | Black | Red | Orange | Green | Blue | Black |
| Color development assisting agent test ink Type E | XX | X | X | XX | X | X | X | X | X | X |

◎ Dark, quick;
○ good;
△ pale, slow;
X very pale;
XX not colored

The results were "pale" or "not colored" in all the colors of indicator test ink of both of types A and B. It has been confirmed that in order to obtain a vivid color, some kind of additive needs to be used.

Experiment 2

Experiment 2 was conducted to check the effect of a surfactant as the additive, more specifically the effect provided by incorporating a surfactant into the indicator test ink but not into the color development assisting agent.

The indicator test ink of type C was applied to a back sheet to form an indicator portion. The color development assisting agent test ink of type E was applied to crepe paper and dried to form a color development assisting agent test paper sheet. The color development assisting agent test paper sheet was put on the above-formed indicator portion, and water of 36° C. was dropped thereto. It was determined whether or not a vivid color appeared immediately. Ten types of color development assisting agent test paper sheets containing different surfactants were prepared. The difference among these test paper sheets was also checked.

The results are as shown in Table 18. The color development results are different in accordance with the surfactant and the color, but no sample resulted in "not colored". Namely, occurrence of color development was recognized in all the cases.

TABLE 18

Indicator test ink Type C
Numeral in < > represents the type of surfactant

|  | <1> | <2> | <3> | <4> | <5> | <6> | <7> | <8> | <9> | <10> |
|---|---|---|---|---|---|---|---|---|---|---|
| Red | ○ | ◎ | ○ | Δ | Δ | X | X | X | Δ | X |
| Orange | ◎ | ○ | ○ | ○ | ○ | Δ | ○ | Δ | ○ | X |
| Green | ◎ | ◎ | ○ | ○ | ○ | Δ | Δ | Δ | ○ | Δ |
| Blue | ◎ | ◎ | ○ | Δ | Δ | X | Δ | X | Δ | X |
| Black | ◎ | ○ | ○ | Δ | Δ | Δ | Δ | X | ○ | X |

◎ Dark, quick;
○ good;
Δ pale, slow;
X very pale;
XX not colored

Experiment 3

Experiment 3 was conducted to check the effect of the surfactant as the additive, more specifically the effect provided by incorporating a surfactant into the color development assisting agent but not into the indicator test ink.

The indicator test ink of type A was applied to a back sheet to form an indicator portion. The indicator test ink of type B was applied to a back sheet to form an indicator portion. The color development assisting agent test ink of type D was applied to crepe paper and dried to form a color development assisting agent test paper sheet. The color development assisting agent test paper sheet was put on each of the above-formed indicator portions, and water of 36° C. was dropped thereto. It was determined whether or not a vivid color appeared immediately. Ten types of color development assisting agent test paper sheets containing different surfactants were prepared. The difference among these test paper sheets was also checked.

The results are as shown in Table 19.

Experiment 4

Experiment 4 was conducted to check the difference in the color development state caused by the difference in the color-developing agent and the color development assisting agent. The indicator test ink used was prepared to contain 25 parts by weight of ethyl acetate, 43 parts by weight of IPA, 20 parts by weight of DMF, 10 parts by weight of surfactant and remaining 2 parts by weight of color-developing agent. As the surfactant, "polyoxyethylenedistyrenated phenylether" (2nd in the nonionic surfactant list; see Table 13) (trade name: Emulgen A60 produced by Kao Corporation) was used. Such indicator test ink will be referred to as "C-1".

61 types of color-developing agents (see Tables 1 through 12) were independently used to obtain 61 types of indicator test ink.

Each type of indicator test ink was applied to a back sheet and dried to create 61 types of back sheets each including the indicator portion.

The color development assisting agent test ink was prepared to contain 35 parts by weight of ethanol, 45 parts by

TABLE 19

| | | Indicator test ink Type A, Type B | | | | | | | | | |
|---|---|---|---|---|---|---|---|---|---|---|---|
| | | Type A | | | | | Type B | | | | |
| | | Red | Orange | Green | Blue | Black | Red | Orange | Green | Blue | Black |
| Color development | D<1> | XX | X | X | X | X | X | X | X | X | X |
| assisting agent test ink | D<2> | XX | X | X | XX | X | X | X | X | X | X |
| Type D | D<3> | XX | X | X | XX | X | X | X | X | X | X |
| Numeral in < > | D<4> | XX | XX | XX | XX | XX | X | X | X | X | X |
| represents the type of | D<5> | XX | X | X | X | X | X | X | X | X | X |
| surfactant | D<6> | XX | XX | XX | XX | XX | X | X | X | X | X |
| | D<7> | XX | XX | XX | XX | XX | X | X | X | X | X |
| | D<8> | XX | XX | XX | XX | XX | X | X | X | X | X |
| | D<9> | XX | XX | X | X | XX | X | X | X | X | X |
| | D<10> | XX | XX | XX | XX | XX | X | X | X | X | X |

◎ Dark, quick;
○ good;
Δ pale, slow;
X very pale;
XX not colored

Color development did occur, but the colors were very pale.

From the results of experiments 1 through 3, it has been found that in order to obtain a vivid color immediately, a surfactant needs to be contained, and that it is preferable that the surfactant is contained in the indicator test ink. Namely, it is desirable to use the indicator test ink of type C (see Table 15) and the color development assisting agent test ink of type E (see Table 16).

weight of IPA, and 20 parts by weight of color development assisting agent. 15 types of color development assisting agents (see Table 14) were independently used to obtain 15 types of color development assisting agent test ink. Such color development assisting agent test ink will be referred to as "E-1".

Each type of color development assisting agent test ink was applied to crepe paper and dried to create 15 types of color development assisting agent test sheets.

The 15 types of color development assisting agent test sheets were each put on the indicator portion of each of the 61 types of back sheets, and water of 36° C. was dropped thereto. It was determined whether or not a vivid color appeared immediately.

The results are as shown in Tables 20 through 25.

TABLE 20

Indicator test ink C-1
Numeral in < > represents the type of color-developing agent
Red

| | | <1> | <2> | <3> | <4> | <5> | <6> | <7> | <8> | <9> | <10> | <11> |
|---|---|---|---|---|---|---|---|---|---|---|---|---|
| Color development assisting agent test ink E-1 Numeral in < > represents the type of color development assisting agent | E <1> | Δ | ◯ | ◯ | ◯ | ◯ | ◯ | ◉ | Δ | Δ | ◯ | ◯ |
| | E <2> | ◯ | ◯ | ◯ | ◯ | ◯ | ◯ | ◉ | ◯ | Δ | ◯ | ◯ |
| | E <3> | ◯ | ◯ | ◯ | ◯ | ◯ | ◯ | ◉ | ◯ | Δ | ◯ | ◯ |
| | E <4> | X | Δ | X | X | Δ | X | ◯ | X | ◯ | X | XX |
| | E <5> | X | Δ | X | X | Δ | X | Δ | X | X | X | XX |
| | E <6> | XX | XX | XX | XX | X | XX | Δ | XX | X | XX | XX |
| | E <7> | X | ◯ | Δ | Δ | ◯ | Δ | ◉ | X | ◯ | Δ | X |
| | E <8> | XX | Δ | Δ | Δ | Δ | Δ | ◯ | XX | ◯ | Δ | Δ |
| | E <9> | X | X | XX | XX | Δ | XX | Δ | XX | Δ | XX | XX |
| | E <10> | Δ | ◯ | Δ | Δ | ◯ | Δ | ◉ | Δ | ◯ | Δ | Δ |
| | E <11> | XX | XX | XX | XX | X | XX | Δ | XX | X | XX | XX |
| | E <12> | XX | XX | XX | XX | XX | XX | XX | XX | XX | XX | XX |
| | E <13> | X | Δ | X | X | Δ | X | ◯ | X | ◯ | Δ | Δ |
| | E <14> | XX | XX | XX | XX | XX | XX | XX | XX | XX | XX | XX |
| | E <15> | Δ | ◯ | Δ | Δ | ◯ | Δ | ◯ | Δ | ◯ | Δ | Δ |

◉ Dark, quick;
◯ good;
Δ pale, slow;
X very pale;
XX not colored

TABLE 21

Indicator test ink C-1
Numeral in < > represents the type of color-developing agent

| | | Orange | | | Yellow | | | | Green | | | |
|---|---|---|---|---|---|---|---|---|---|---|---|---|
| | | <12> | <13> | <14> | <15> | <16> | <17> | <18> | <19> | <20> | <21> | <22> |
| Color development assisting agent test ink E-1 Numeral in < > represents the type of color development assisting agent | E <1> | ◯ | ◯ | ◯ | X | XX | XX | XX | ◯ | ◉ | ◯ | ◯ |
| | E <2> | ◯ | ◯ | ◯ | ◯ | X | XX | ◯ | ◯ | ◉ | ◯ | ◯ |
| | E <3> | ◯ | ◯ | ◯ | X | XX | XX | XX | ◯ | ◉ | ◯ | ◯ |
| | E <4> | ◯ | X | X | XX | XX | XX | ◯ | ◯ | ◯ | X | XX |
| | E <5> | Δ | XX | X | X | X | XX | Δ | Δ | Δ | XX | XX |
| | E <6> | XX | XX | XX | XX | XX | XX | XX | X | Δ | XX | XX |
| | E <7> | ◯ | Δ | Δ | ◯ | ◯ | ◯ | ◯ | ◯ | ◯ | Δ | XX |
| | E <8> | ◯ | X | Δ | X | XX | XX | ◯ | Δ | Δ | X | XX |
| | E <9> | X | X | XX | XX | XX | XX | XX | Δ | Δ | XX | XX |
| | E <10> | ◯ | Δ | Δ | Δ | X | X | ◯ | ◯ | ◯ | Δ | XX |
| | E <11> | X | XX | XX | XX | XX | XX | XX | XX | X | XX | X |
| | E <12> | XX | XX | XX | XX | XX | XX | XX | XX | X | XX | XX |
| | E <13> | Δ | Δ | Δ | ◯ | XX | XX | ◯ | ◯ | Δ | X | XX |
| | E <14> | XX | XX | XX | XX | XX | XX | XX | X | X | XX | XX |
| | E <15> | ◯ | ◯ | Δ | X | X | XX | ◯ | ◯ | ◯ | Δ | XX |

◉ Dark, quick;
◯ good;
Δ pale, slow;
X very pale;
XX not colored

TABLE 22

Indicator test ink C-1
Numeral in < > represents the type of color-developing agent

| | | Green | | | | Blue | | | | | | |
|---|---|---|---|---|---|---|---|---|---|---|---|---|
| | | <23> | <24> | <25> | <26> | <27> | <28> | <29> | <30> | <31> | <32> | <33> |
| Color development assisting agent test ink E-1 | E <1> | ◉ | ◉ | ◉ | ◉ | ◯ | ◯ | ◯ | ◯ | ◯ | ◉ | ◯ |
| | E <2> | ◉ | ◉ | ◉ | ◉ | ◯ | ◯ | ◯ | ◯ | ◯ | ◉ | ◯ |
| | E <3> | ◉ | ◉ | ◉ | ◉ | ◯ | ◯ | ◯ | ◯ | ◯ | ◉ | ◯ |

TABLE 22-continued

Indicator test ink C-1
Numeral in < > represents the type of color-developing agent

|  |  | Green | | | | Blue | | | | | | |
|---|---|---|---|---|---|---|---|---|---|---|---|---|
|  |  | <23> | <24> | <25> | <26> | <27> | <28> | <29> | <30> | <31> | <32> | <33> |
| Numeral in < > represents the type of color development assisting agent | E <4> | ○ | ○ | ○ | X | X | XX | XX | X | Δ | ○ | XX |
| | E <5> | Δ | Δ | ○ | X | X | XX | XX | XX | X | Δ | XX |
| | E <6> | X | X | ○ | X | XX | XX | XX | XX | XX | X | XX |
| | E <7> | ○ | ○ | ○ | XX | X | XX | X | X | XX | ◎ | X |
| | E <8> | Δ | Δ | Δ | Δ | X | XX | XX | XX | Δ | ○ | XX |
| | E <9> | Δ | Δ | ○ | X | XX | XX | XX | XX | X | Δ | XX |
| | E <10> | ○ | ○ | ○ | X | XX | XX | XX | Δ | X | ◎ | XX |
| | E <11> | X | X | ○ | X | XX | XX | XX | XX | XX | X | XX |
| | E <12> | X | X | Δ | XX | XX | XX | XX | XX | XX | XX | XX |
| | E <13> | Δ | Δ | Δ | Δ | XX | XX | XX | X | Δ | ○ | XX |
| | E <14> | X | X | Δ | XX | XX | XX | XX | XX | XX | XX | XX |
| | E <15> | ○ | ○ | ○ | Δ | X | XX | X | X | X | ○ | X |

◎ Dark, quick;
○ good;
Δ pale, slow;
X very pale;
XX not colored

TABLE 23

Indicator test ink C-1
Numeral in < > represents the type of color-developing agent
Black

|  |  | <34> | <35> | <36> | <37> | <38> | <39> | <40> | <41> | <42> | <43> | <44> |
|---|---|---|---|---|---|---|---|---|---|---|---|---|
| Color development assisting agent test ink E-1 Numeral in < > represents the type of color development assisting agent | E <1> | ○ | ○ | ○ | ◎ | Δ | ○ | ○ | ○ | ◎ | ◎ | ◎ |
| | E <2> | ○ | ○ | ◎ | ◎ | ○ | ○ | ○ | ◎ | ◎ | ◎ | ◎ |
| | E <3> | ○ | ○ | ○ | ◎ | ○ | ○ | ○ | ○ | ◎ | ◎ | ◎ |
| | E <4> | ○ | ○ | Δ | ○ | Δ | ○ | ○ | Δ | ○ | ○ | ○ |
| | E <5> | Δ | Δ | X | ○ | X | ○ | ○ | X | X | ○ | ○ |
| | E <6> | X | X | X | ○ | X | X | X | X | X | ○ | Δ |
| | E <7> | ○ | ○ | Δ | ○ | Δ | ○ | ○ | Δ | ○ | ○ | ○ |
| | E <8> | ○ | ○ | Δ | Δ | Δ | Δ | ○ | Δ | Δ | Δ | Δ |
| | E <9> | Δ | Δ | Δ | Δ | Δ | Δ | Δ | Δ | Δ | ○ | ○ |
| | E <10> | ○ | ○ | ○ | ○ | ◎ | ○ | ○ | ○ | ○ | ○ | ○ |
| | E <11> | X | X | X | X | XX | XX | X | X | X | X | X |
| | E <12> | XX | XX | Δ | ○ | X | XX | XX | Δ | Δ | Δ | Δ |
| | E <13> | ○ | ○ | Δ | Δ | Δ | ○ | ○ | Δ | Δ | Δ | Δ |
| | E <14> | XX | XX | X | X | X | X | XX | X | X | X | ○ |
| | E <15> | ○ | ○ | ○ | ○ | ○ | ○ | ○ | ○ | ○ | ○ | ○ |

◎ Dark, quick;
○ good;
Δ pale, slow;
X very pale;
XX not colored

TABLE 24

Indicator test ink C-1
Numeral in < > represents the type of color-developing agent

|  |  | Red | | | | | | | | Orange | Yellow | Green |
|---|---|---|---|---|---|---|---|---|---|---|---|---|
|  |  | <45> | <46> | <47> | <48> | <49> | <50> | <51> | <52> | <53> | <54> | <55> |
| Color development assisting agent test ink E-1 Numeral in < > represents the type of color development assisting agent | E <1> | ○ | ○ | ○ | Δ | ○ | Δ | Δ | ○ | ○ | Δ | ○ |
| | E <2> | ◎ | ○ | ◎ | ○ | ○ | ○ | ○ | ◎ | ○ | Δ | ○ |
| | E <3> | ○ | ○ | ○ | ○ | ○ | ○ | ○ | ○ | ○ | Δ | ○ |
| | E <4> | X | X | X | X | Δ | X | X | Δ | X | X | ○ |
| | E <5> | X | XX | X | XX | X | XX | XX | X | X | X | Δ |
| | E <6> | XX | XX | X | XX | X | XX | XX | XX | XX | XX | X |
| | E <7> | ○ | Δ | Δ | X | Δ | X | Δ | Δ | Δ | Δ | ○ |
| | E <8> | X | XX | XX | XX | XX | XX | XX | ○ | X | Δ | Δ |
| | E <9> | Δ | X | X | X | XX | XX | XX | Δ | X | X | Δ |
| | E <10> | ○ | ○ | ◎ | Δ | Δ | Δ | Δ | ◎ | Δ | Δ | ○ |
| | E <11> | XX | XX | XX | XX | XX | XX | XX | XX | XX | XX | XX |
| | E <12> | XX | XX | X | XX | XX | XX | XX | XX | XX | XX | XX |

TABLE 24-continued

Indicator test ink C-1
Numeral in < > represents the type of color-developing agent

|  |  | Red | | | | | | | | Orange | Yellow | Green |
|---|---|---|---|---|---|---|---|---|---|---|---|---|
|  |  | <45> | <46> | <47> | <48> | <49> | <50> | <51> | <52> | <53> | <54> | <55> |
|  | E <13> | ○ | Δ | Δ | X | Δ | X | X | ○ | Δ | Δ | ○ |
|  | E <14> | X | XX | XX | XX | XX | XX | XX | Δ | XX | X | X |
|  | E <15> | ○ | ○ | ◎ | Δ | ○ | Δ | Δ | ◎ | ○ | Δ | ○ |

◎ Dark, quick;
○ good;
Δ pale, slow;
X very pale;
XX not colored

TABLE 25

Indicator test ink C-1
Numeral in < > represents the
type of color-developing agent

|  |  | Green | | Blue | | Black | |
|---|---|---|---|---|---|---|---|
|  |  | <56> | <57> | <58> | <59> | <60> | <61> |
| Color development | E <1> | ○ | ○ | ○ | ○ | ○ | Δ |
| assisting agent test | E <2> | ○ | ○ | ○ | ◎ | ○ | ○ |
| ink E-1 | E <3> | ○ | ○ | ○ | ○ | ○ | ○ |
| Numeral in < > | E <4> | X | X | X | Δ | ○ | Δ |
| represents the type | E <5> | XX | X | XX | X | XX | XX |
| of color | E <6> | XX | X | XX | XX | XX | XX |
| development | E <7> | Δ | XX | XX | X | Δ | Δ |
| assisting agent | E <8> | X | Δ | X | X | Δ | Δ |
|  | E <9> | XX | X | XX | X | Δ | Δ |
|  | E <10> | Δ | X | X | Δ | ○ | ◎ |
|  | E <11> | XX | XX | XX | XX | XX | XX |
|  | E <12> | XX | XX | XX | XX | XX | XX |
|  | E <13> | X | Δ | X | Δ | ○ | Δ |
|  | E <14> | XX | XX | XX | XX | X | X |
|  | E <15> | Δ | Δ | X | Δ | ○ | ○ |

◎ Dark, quick;
○ good;
Δ pale, slow;
X very pale;
XX not colored

The results were generally as follows regarding the indicator test ink C-1 although there were some variances. Among the color-developing agents for red, "3,3-bis(1-n-butyl-2-methyl-indoyl-3)phthalate" (7th; see Table 1) resulted in a good coloration reaction relatively regardless of the type of the color development assisting agent. As can be seen, it is preferable to use, for orange, "1,3-dimethyl-6-diethylaminofluoran" (12th; see Table 2); for green, "3,3-bis(4-diethylmino-2-ethoxyphenyl)-4-azaphthalide" (26th; see Table 4); and for blue, "3-(4-diethylamino-2-ethoxyphenyl)-3-(1-ethyl-2-methylindoyl-3)-4-azaphthalide" (32nd; see Table 5).

It can be seen that for forming the color development assisting agent test ink, it is preferable to use, as the color development assisting agent, "tannic acid" (1st in Table 14), "gallic acid" (2nd in Table 14), "propyl gallate" (3rd in Table 14), "citric acid" (7th in Table 14), "tartaric acid" (10th in Table 14) or "malic acid" (15th in Table 14). When each of these color development assisting agents is used, a relatively wide range of color-developing agents are caused to develop a color to a high degree. Namely, a plurality of color-developing agents are caused to develop a color with a single color development assisting agent.

Tannic acid, gallic acid and propyl gallate are polyphenols, and thus are expected to provide an effect of deodorizing the excrements. These substances also have an antibacterial function. A color development assisting agent provide a function thereof when being dissolved. Polyphenol is derived from a naturally occurring substance and thus is safe.

For reference, substantially the same experiments were conducted by use of water of a temperature higher than 36° C., specifically of 80° C. Good color development was recognized to have occurred even under the conditions which exhibited "x" in Tables 20 through 25.

Experiment 5

In experiment 5, the indicator test ink C-1 using the color-developing agents for red, orange, green and blue, which exhibited good results in experiments 4, and the color development assisting agent test ink E-1 ("tannic acid" (1st in Table 14), "gallic acid" (2nd in Table 14), "propyl gallate" (3rd in Table 14), "citric acid" (7th in Table 14), "tartaric acid" (10th in Table 14) and "malic acid" (15th in Table 14)), which also exhibited good results in experiments 4, were used. The indicator test ink of each color was applied to a back sheet by gravure printing (printing plate depth: 20 μm), as one example of application, to form an indicator portion. In order to check whether or not a mixed color would vividly appear, the indicator test ink C-1 containing a mixture of color-developing agents for red and blue was also prepared.

The above-mentioned six types of color development assisting agent test paper sheets were each put on the indicator portion of each of the five types of back sheets, and water of 36° C. was dropped thereto, in the same manner as described above. It was determined whether or not a vivid color appeared immediately.

The results are as shown in Table 26.

TABLE 26

Indicator test ink C-1
Numeral in < > represents the
type of color-developing agent

|  |  | Red <7> | Orange <12> | Green <26> | Blue <32> | Purple <7, 32> |
|---|---|---|---|---|---|---|
| Color development | E <1> | ◎ | ◎ | ◎ | ◎ | ◎ |
| assisting agent | E <2> | ◎ | ○ | ○ | ◎ | ○ |
| test ink E-1 | E <3> | ◎ | ◎ | ◎ | ◎ | ◎ |
| Numeral in < > | E <7> | ○ | ○ | X | ○ | ○ |
| represents the type | E <10> | ○ | ○ | X | ○ | ○ |
| of color | E <15> | ○ | ○ | X | ○ | ○ |
| development assisting agent |  |  |  |  |  |  |

◎ Dark, quick;
○ good;
Δ pale, slow;
X very pale;
XX not colored

It has been confirmed that the indicator portion is formed by gravure printing and that a good color development state is obtained in almost all the types of indicator test ink C-1 including the indicator test ink C-1 for purple obtained by mixing red and blue.

Experiment 6

Experiment 6 was conducted to check whether or not a good color development state would be obtained with cotton containing a color development assisting agent absorbed thereto instead of a color development assisting agent test paper sheet. As in experiment 5, the indicator test ink C-1 using the color-developing agents for red, orange, green and blue, which exhibited good results in experiments 4, and the color development assisting agent test ink E-1 ("tannic acid" (1st in Table 14), "gallic acid" (2nd in Table 14), "propyl gallate" (3rd in Table 14), "citric acid" (7th in Table 14), "tartaric acid" (10th in Table 14) and "malic acid" (15th in Table 14)), which also exhibited good results in experiments 4, were used. The indicator test ink of each color was applied to a back sheet by gravure printing to form an indicator portion. The indicator test ink C-1 containing a mixture of color-developing agents for red and blue was also prepared to form an indicator portion.

The color development assisting agent was absorbed to (immersed in) absorptive cotton and dried. The absorptive cotton containing the color development assisting agent absorbed thereto was put on the indicator portion of each of the five types of back sheets, and water of 36° C. was dropped thereto. It was determined whether or not a vivid color appeared immediately.

The results are as shown in Table 27.

TABLE 27

| | | Indicator test ink C-1 Numeral in < > represents the type of color-developing agent | | | | |
|---|---|---|---|---|---|---|
| | | Red <7> | Orange <12> | Green <26> | Blue <32> | Purple <7, 32> |
| Color development assisting agent test ink E-1 Numeral in < > represents the | E <1> | ◎ | ○ | ◎ | ◎ | ◎ |
| | E <2> | ○ | ○ | ○ | ○ | ○ |
| | E <3> | ◎ | ○ | ◎ | ◎ | ○ |
| | E <7> | ○ | ○ | X | ○ | ○ |
| | E <10> | ○ | ○ | X | ○ | ○ |

TABLE 27-continued

| | | Indicator test ink C-1 Numeral in < > represents the type of color-developing agent | | | | |
|---|---|---|---|---|---|---|
| | | Red <7> | Orange <12> | Green <26> | Blue <32> | Purple <7, 32> |
| type of color development assisting agent | E <15> | ○ | ○ | X | ○ | ○ |

◎ Dark, quick;
○ good;
Δ pale, slow;
X very pale;
XX not colored

Although the results are partially inferior to those of experiment 5, substantially the same color development state was obtained as a whole.

Substantially the same experiment was conducted with an absorption body containing each of the color development assisting agents in a powder form mixed therein. The results were substantially the same as those in Table 27.

From these results, it is understood that the same effect is provided even when the color development assisting agent is directly mixed.

Experiment 7

Experiment 7 was conducted to check the difference in the color development state caused by the difference in the printing plate depth and the liquid amount, and also to check a coloration reaction obtained by actual urine. Like in experiment 5, the indicator test ink C-1 for each of red, orange, green, blue and purple was used. The gravure printing on the back sheets was performed by use of four types of printing plates having depths of 20 µm, 18 µm, 16 µm and 14 µm. Thus, indicator portions having different thicknesses were obtained. As shown in FIG. 1, each indicator portion was formed in the entirety of the absorption body area.

As the color development assisting agent, a mixture of "tannic acid" (let in Table 14) and "propyl gallate" (3rd), among those which exhibited good results in experiment 4, was prepared. Thus, the color development assisting agent test paper sheet was obtained. The color development assisting agent test ink contained 35 parts by weight of ethanol, 45 parts by weight of IPA, 10 parts by weight of tannic acid, and 10 parts by weight of propyl gallate.

The color development assisting agent test paper sheet was put on the indicator portion of the back sheet of each of the four thicknesses and each color, and each resultant back sheet was attached to a commercially available paper diaper at a position where the back sheet would be attached. Then, urine of 36° C. was dropped thereto. It was determined whether or not a vivid color appeared immediately. Urine was dropped in four different amounts of 30 cc, 50 cc, 70 cc and 90 cc.

The results are as shown in Table 28.

TABLE 28

| | | Indicator test ink C-1 Numeral in < > represents the type of color-developing agent | | | | | | | | | | | | | | | | | | |
|---|---|---|---|---|---|---|---|---|---|---|---|---|---|---|---|---|---|---|---|---|
| Amount used (cc) | Amount reaching ink (cc) | Red <7> Printing plate depth (µm) | | | | Orange <12> Printing plate depth (µm) | | | | Green <26> Printing plate depth (µm) | | | | Blue <32> Printing plate depth (µm) | | | | Purple <7, 32> Printing plate depth (µm) | | | |
| | | 20 | 18 | 16 | 14 | 20 | 18 | 16 | 14 | 20 | 18 | 16 | 14 | 20 | 18 | 16 | 14 | 20 | 18 | 16 | 14 |
| 30 | 4~10 | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ |
| 50 | 12~20 | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ |

TABLE 28-continued

| | | Indicator test ink C-1 Numeral in < > represents the type of color-developing agent ||||||||||||||||||||
| Amount used (cc) | Amount reaching ink (cc) | Red <7> Printing plate depth (μm) |||| Orange <12> Printing plate depth (μm) |||| Green <26> Printing plate depth (μm) |||| Blue <32> Printing plate depth (μm) |||| Purple <7, 32> Printing plate depth (μm) ||||
| | | 20 | 18 | 16 | 14 | 20 | 18 | 16 | 14 | 20 | 18 | 16 | 14 | 20 | 18 | 16 | 14 | 20 | 18 | 16 | 14 |
|---|---|---|---|---|---|---|---|---|---|---|---|---|---|---|---|---|---|---|---|---|---|
| 70 | 24~35 | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ |
| 90 | 40~60 | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ | ◎ |

◎ Dark, quick;
○ good;
Δ pale, slow;
X very pale;
XX not colored
* Indicator test ink was gravure-printed.
For the color development assisting agent test ink, E-1 <1, 3> was used.

Figure 6:
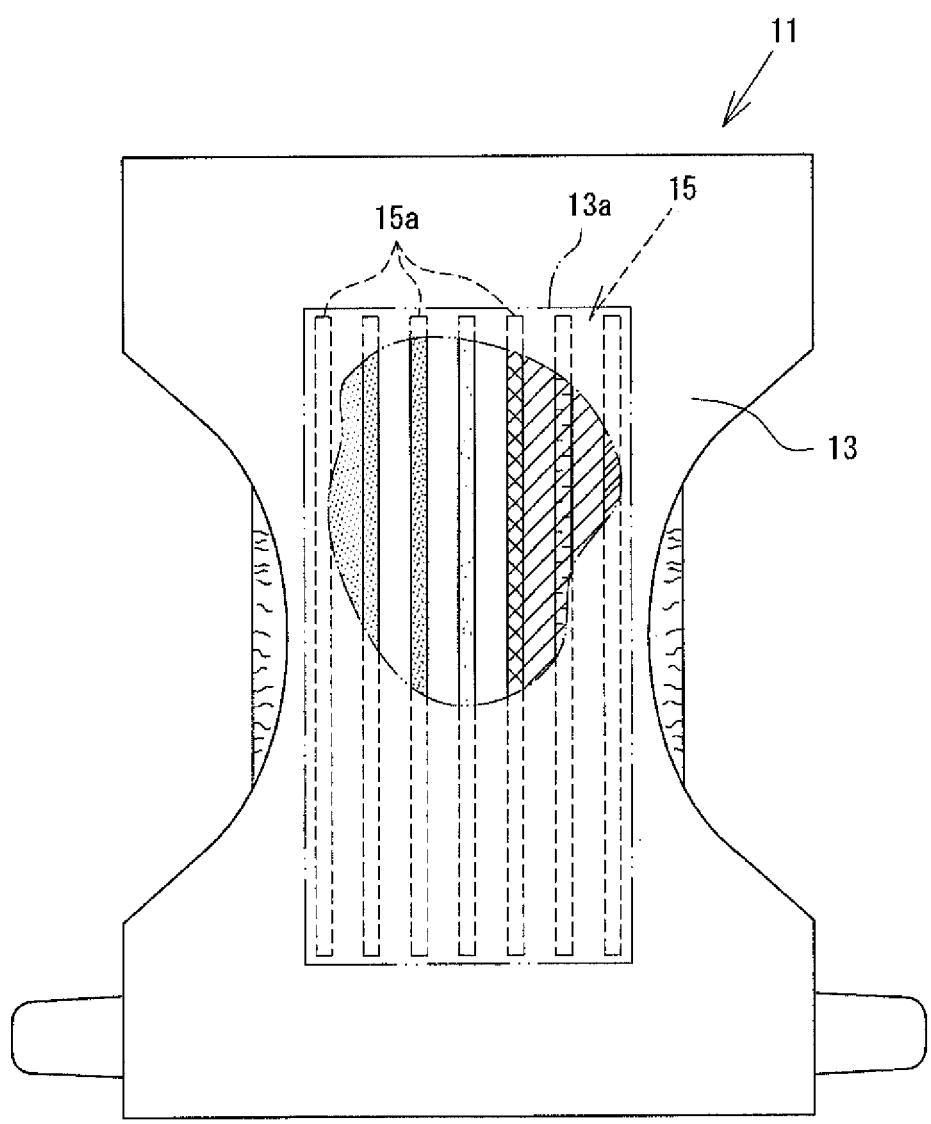
FIG. 6 is a schematic plan view showing an outer surface of a paper diaper in a functioning state.

In all the cases, a vivid color was obtained. FIG. 6 shows the color development state. In FIG. 6, different patterns represent different colors.

After the color development, the back sheets were left as they were. Even one day later, and two days later, each color was not faded and was kept vivid. As the amount of urine was larger, the range of colors was wider.

From these results, it is understood that a good color development state is obtained regardless of the thickness of the indicator portion; that a quick and clear coloration reaction occurs even with actual urine; that it is effective to mix a plurality of types of color development assisting agents; that once developed, the color is not easily faded; that the color is developed even when the amount of urine is small; and the range of developed colors is in accordance with the amount of urine.

Experiment 8

In experiment 8, it was checked whether or not the effect would be provided when the indicator test ink was applied to the back sheet by flexo printing as one example of application instead of gravure printing.

The experiment was conducted in substantially the same manner as in experiment 7 except that the indicator portions had the same thickness.

The results are as shown in Table 29.

TABLE 29

| Indicator test ink C-1 Numeral in < > represents the type of color-developing agent |||||
| Red <7> | Orange <12> | Green <26> | Blue <32> | Purple <7, 32> |
|---|---|---|---|---|
| ◎ | ◎ | ◎ | ◎ | ◎ |

◎ Dark, quick;
○ good;
Δ pale, slow;
X very pale;
XX not colored
* Indicator test ink was flexo-printed.
For the color development assisting agent test ink, E-1 <1, 3> was used.

It has been confirmed that the indicator portion can be formed by flexo printing. In all the cases, a vivid color was obtained. As can seen from this, there is no problem with the color development.

Experiment 9

Experiment 9 was conducted to check the difference in the color development state between the indicator test ink which permeates to the other side of the back sheet and the indicator test ink which does not permeate to the other side of the back sheet.

Indicator test ink having the compositions shown in Table 30 was used.

TABLE 30

| | | Composition of indicator test ink ||||||||
| | | A-2 || B-2 || C-2 ||||
| | | Green <26> | Blue <32> | Green <26> | Blue <32> | Green <26> | Blue <32> | Red <7> | Orange <12> |
|---|---|---|---|---|---|---|---|---|---|
| Ethyl acetate | | | | | | 25 | 25 | 25 | 25 |
| Methyl acetate | | | | 25 | 25 | | | | |
| Ethanol | | 25 | 25 | | | | | | |
| IPA | | 43 | 43 | 43 | 43 | 43 | 43 | 43 | 43 |
| DMF | | 20 | 20 | 20 | 20 | 20 | 20 | 20 | 20 |
| Color-developing agent | Green <26> | 2 | | 2 | | 2 | | | |
| | Blue <32> | | 2 | | 2 | | 2 | | |
| | Red <7> | | | | | | | 2 | |
| | Orange <12> | | | | | | | | 2 |
| Surfactant | | 10 | 10 | 10 | 10 | 10 | 10 | 10 | 10 |

*A: ink permeates to the other side; B and C: ink does not permeate to the other side.
For the color development assisting agent test ink, E-1 <1, 3> is used.

As the indicator test ink which permeates to the other side of the back sheet, ink containing solvents of ethanol, IPA and DMF like the indicator test ink of type A (see Table 15) was prepared. Based on the results of experiments 1 through 3, a surfactant was incorporated.

The indicator test ink contained 25 parts by weight of ethanol, 43 parts by weight of IPA, 20 parts by weight of DMF, 10 parts by weight of surfactant, and 2 parts by weight of color-developing agent. Green and blue color-developing agents, which exhibited good results in experiment 4, were used. Such indicator test ink will be referred to as "A-2".

As the indicator test ink which does not permeate to the other side of the back sheet, ink containing a mixture of solvents for expanding the minute holes in the back sheet like the indicator test ink of types B and C (see Table 15) was used. In these cases also, a surfactant was incorporated.

The indicator test ink similar to the indicator test ink of type B contained 25 parts by weight of methyl acetate, 43 parts by weight of IPA, 20 parts by weight of DMF, 10 parts by weight of surfactant, and 2 parts by weight of color-developing agent. This indicator test ink will be referred to as "B-2".

The indicator test ink similar to indicator test ink of type C contained 25 parts by weight of ethyl acetate, 43 parts by weight of IPA, 20 parts by weight of DMF, 10 parts by weight of surfactant, and 2 parts by weight of color-developing agent. This indicator test ink will be referred to as "C-2".

As the indicator test ink of each of A-2 and B-2, the indicator test ink for green and blue (two colors) was used. As the indicator test ink of C-2, the indicator test ink for green, blue, red and orange (four colors) was used.

The indicator test ink of each of types A-2, B-2 and C-2 was applied to a back sheet to form an indicator portion. The indicator portion was formed in the entirety of the absorption body area.

As the color development assisting agent, a mixture of "tannic acid" (1st in Table 14) and "propyl gallate" (3rd), among those which exhibited good results in experiment 4, was prepared. Thus, the color development assisting agent test paper sheet was obtained. The color development assisting agent test ink contained 35 parts by weight of ethanol, 45 parts by weight of IPA, 10 parts by weight of tannic acid, and 10 parts by weight of propyl gallate.

The color development assisting agent test paper sheet was put on the indicator portion of each type of back sheets for each color, and each of the resultant back sheets was attached to a commercially available paper diaper at a position where the back sheet would be attached. Then, urine of 36° C. was dropped thereto. It was determined whether or not a vivid color appeared immediately.

In all the indicator portions formed of the indicator test ink of types A-2, B-2 and C-2, good color development was confirmed. Especially in the indicator portion of the indicator test ink of type A-2, the color was vivid and the profile of the color-developed part was clear. However, a small amount of water permeated.

In the indicator portion of the indicator test ink of types B-2 and C-2, no water permeated, but the color was visible through the back sheet. Although this causes no problem for use, these indicator portions were considered to be slightly inferior to the indicator portion of the indicator test ink of type A-2 in the aspect of aesthetics of appearance.

From these results, the following is understood. In the case where a clear color is desired, it is preferable that ethyl acetate or methyl acetate is not incorporated into the ink used to form the indicator portion. In the case where it is important to prevent leakage of the liquid, it is preferable that ethyl acetate or methyl acetate is incorporated into the ink used to form the indicator portion.

According to the paper diaper having the above-described structure, the color development assisting agent is dissolved in the discharged urine and contacts the indicator portion. Owing to the coloration reaction, the indicator portion, which has been colorless, is colored immediately. Since the color is not faded soon, a wrong recognition on whether the wearer of the paper diaper has urinated or not can be prevented.

Since the indicator portion is colored from a colorless state, it can be clearly determined whether or not the wearer has urinated. The indicator portion is not blotted and a clear and clean color development state is obtained. Thus, the indicator portion can be provided in a large area. Since the reaction occurs even when the amount of urine is very small, the current state of urination can be correctly recognized and an appropriate determination is made.

The indicator portion can be provided in a large area Owing to this, the indicator portion can be provided as having a designed pattern which appears when the wearer has urinated. Thus, the indicator portion can have a novel design. In addition, since the amount of urine can be estimated based on the size of the colored area, the paper diaper can be handled appropriately and is prevented from being replaced unnecessarily.

The color development assisting agent which is dissolved to cause the coloration reaction may be formed of any of many safe substances including polyphenol. An appropriate substance can be chosen easily to provide safety with certainty. Such substances can be used independently or as a combination of a plurality thereof. A coloration reaction of a plurality of color-developing agents can be realized by a single color development assisting agent. Owing to this, the indicator, which has been obtained in a single color conventionally, can be now multi-colored. This realizes a paper diaper which is a fun to see. The works regarding the paper diaper become pleasant for the wearer and also for the care-taker.

Figure 7:
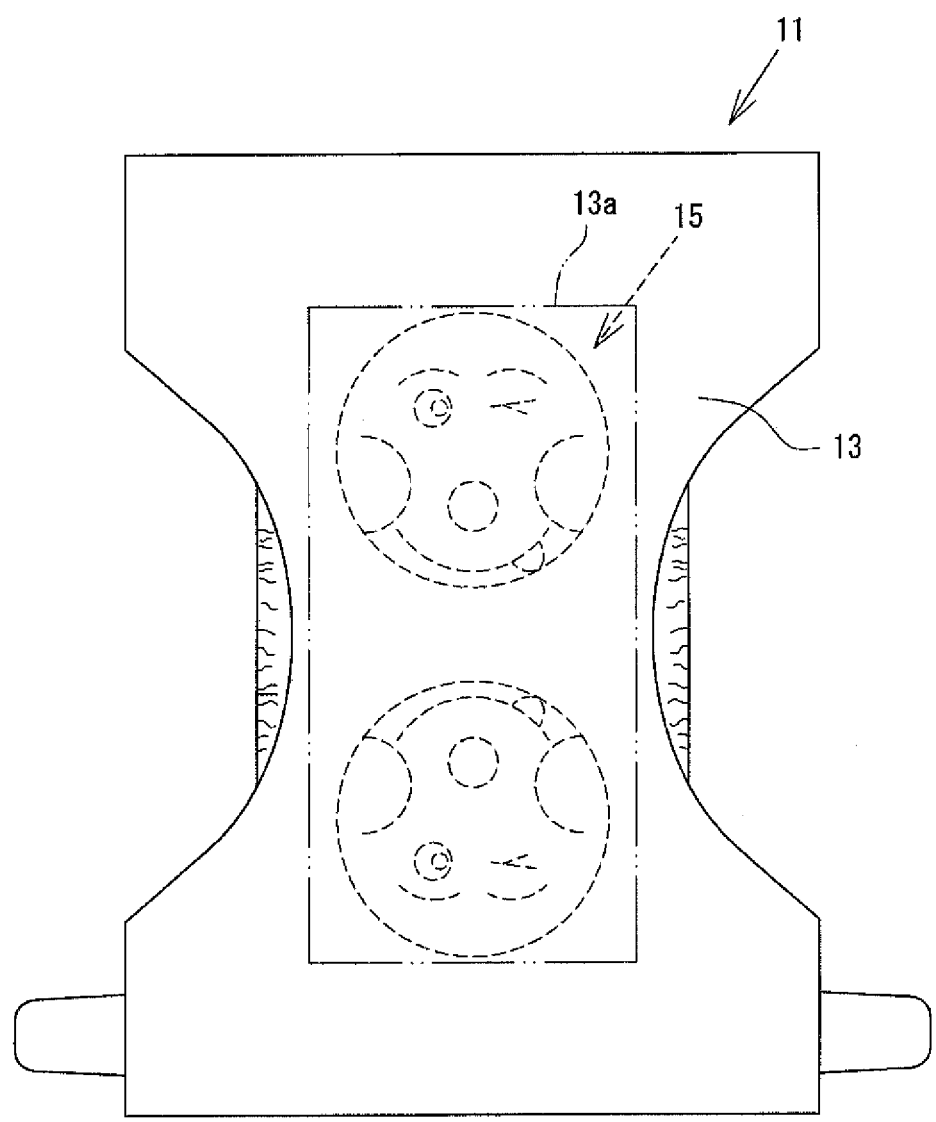
FIG. 7 is a schematic plan view showing an outer surface of a paper diaper in another example.
Figure 8:
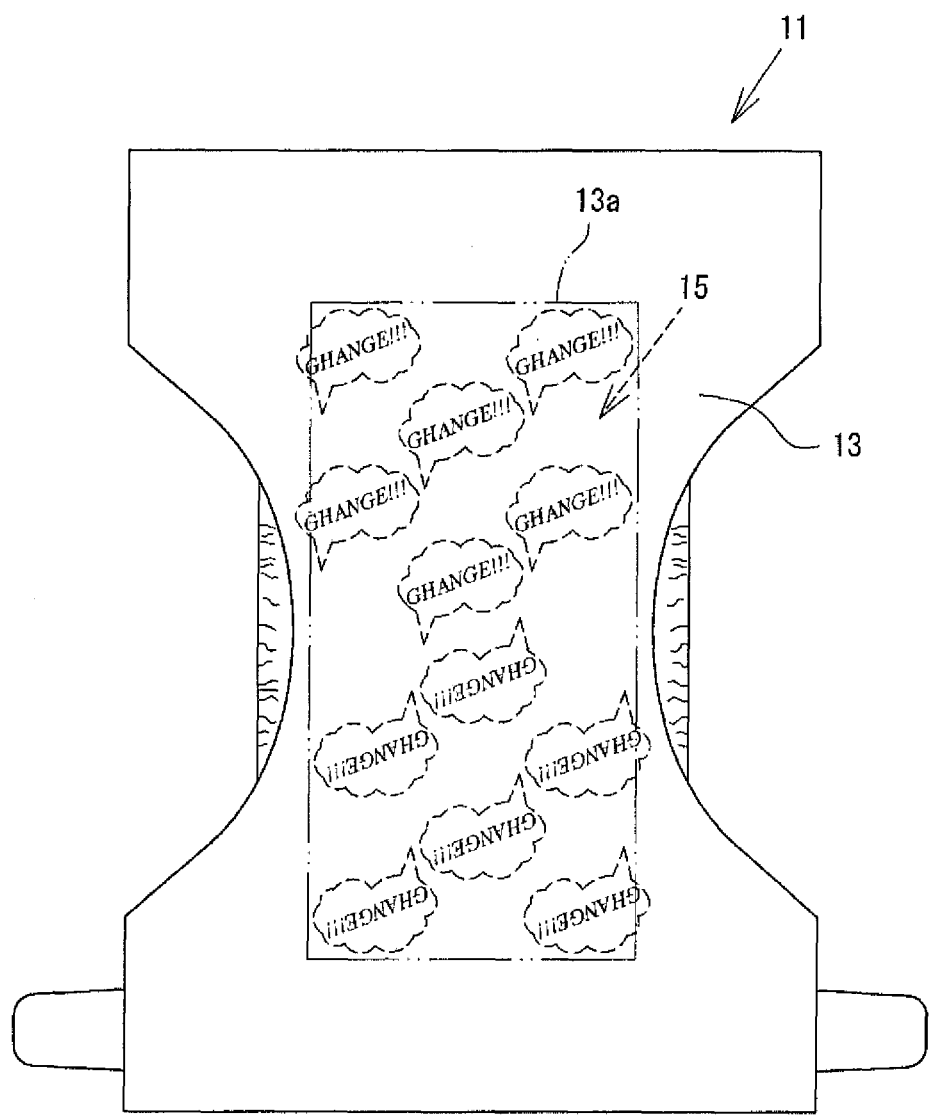
FIG. 8 is a schematic plan view showing an outer surface of a paper diaper in still another example.

FIG. 7 and FIG. 8 are developed plan views each showing a paper diaper including an indicator portion which is pleasant to see and allows the amount of urine to be estimated. The paper diaper shown in FIG. 7 has a graphic pattern of an appropriate character in the indicator portion. The graphic pattern can be provided in multiple colors including red, yellow, black and the like.

The paper diaper shown in FIG. 8 has a designed pattern and letters in the indicator portion. In this case also, the designed pattern and letters can be provided in multiple colors.

One embodiment of the present invention has been described so far. The present invention is not limited to the above-described structure, and any other structure may be adopted.

For example, the indicator portion may be provided in a single color instead of multiple colors.

The indicator portion does not need to be provided in a large area, and may be provided in an area covering the absorption body.

The indicator portion may be structured to provide a pattern which, when being colored, is combined with a designed pattern visible before urination to form a specific graphic pattern or the like.

DESCRIPTION OF THE REFERENCE NUMERALS

11 . . . Paper diaper
13 . . . sack sheet

13a ... Absorption body area
14 ... Absorption body
15 ... Indicator portion
16 ... Color development assisting agent
18 ... Sheet material

What is claimed is:

1. A paper diaper including a back sheet for covering an outer side of an absorption body for absorbing urine, the paper diaper comprising:
   an indicator portion containing a colorless color-developing agent formed of an electron-donating coloration compound, the indicator portion being provided on the back sheet; and
   a color development assisting agent which is activated by water contained in the urine having a temperature of 36° C.±2° C. to contact the indicator portion, thus to cause the indication portion to develop a color, the color development assisting agent being provided in the vicinity of the indicator portion,
   wherein the color development assisting agent is in a powder form and is mixed in the absorption body.

2. A paper diaper according to claim 1, wherein the indicator portion is formed by application or printing performed on a surface of the back sheet, the surface facing the absorption body.

3. A paper diaper according to claim 1, wherein the color development assisting agent is applied or printed adjacent to the indicator portion.

4. A paper diaper according to claim 1, wherein the color-developing agent contains at least one of rhodamine B lactam, 6-diethylamino-benzo[a]fluoran, 3-diethylamino-benzo[a]fluoran, 3-diethylamino-7,8-benzofluoran, 9-diethylamino-benzo[a]fluoran, 3-diethylamino-7-chlorofluoran, 3,3-bis(1-n-butyl-2-methyl-indoyl-3)phthalate, 3,3-bis(1-ethyl-2-methyl-indoyl-3)phthalate, 3,6-bis(diethylamino)fluoran-γ-(4'-nitro) anilinolactam, 3-diethylamino-6-methyl-7-chlorofluoran, 2-bromine-3-methyl-6-dibutylaminofluoran, 1,3-dimethy-6-diethylaminofluoran, 1,3,3-trimethy-indolino-7'-chloro-β-naphthospiropyran, 3-cyclohexylamino-6-chlorofluoran, 2-(phenyliminoethanezyliden)-3,3-trimethylindoline, N-acetylauramine, N-phenylauramine, 2-{2-[4-(dodecyloxy)-3-methoxyphenyl]-ethenyl}quinoline, marachite green lactone, 3-diethylamino-7-dibenzoylaminofluoran, 3-diethylamino-7-chloroanilinofluoran, 3,6,5'-tri(diethylamino)fluorene-9-spiro-1'-(3'-isobenzofuran), 2,N,N-dibenzylamino-6-diethylaminofluoran, 3-(N,N-diethylamino)-7-(N,N-dibenzylamino)fluoran, 3-[2,2-bis(1-ethyl-2-methylindoyl-3)vinyl]-3-(4-diethylaminophenyl)-phthalide, 3,3-bis(4-diethylamino-2-ethoxyphenyl)-4-azaphthalide, crystal violet lactone, ethyl leuco methylene blue, methoxybenzoyl leuco methylene blue, di-β-naphthospiropyran, 3,3-bis(4-diethylaminophenyl)-6-diethylaminophthalide, 3-(4-diethylamino-2-ethoxyphenyl)-3-(1-ethyl-2-methylindoyl-3)-4-azaphthalide, 3-(4-diethylaminophenyl)-3-(1-ethyl-2-methylindoyl-3)-phthalide, 3-cyclohexylmethylamino-6-methyl-7-anilinofluoran, 3-diethylamino-6-methyl-7-anilinofluoran, 3-n-dibutylamino-6-methyl-7-anilinofluoran, 3-diethylamino-6-methyl-7-kylindenofluoran, 2-(2-chloroanilino)-6-diethylaminofluoran, 2-(2-chloroanilino)-6-dibutylaminofluoran, 2-anilino-3-methyl-6-diethyllaminofluoran, 2-anilino-3-methyl-6-dibutylaminofluoran, 6-diethylamino-3-methyl-2-(3-toluideno)-fluoran, 6-diethylamino-3-methyl-2-(2,4-kylindeno)-fluoran, 6-diethylamino-3-methyl-2-(2,6-kylindeno)-fluoran, trade name "S20" produced by Yamamoto Chemicals Inc., trade name "Red 8" produced by Yamamoto Chemicals Inc., trade name "Red 49" produced by Yamamoto Chemicals Inc., trade name "Red 520" produced by Yamada Chemical Co., Ltd., trade name "Red 100" produced by Hodogaya Chemical Co., Ltd., trade name "NC-Red-4" produced by Hodogaya Chemical Co., Ltd., trade name "NC-Red-6" produced by Hodogaya Chemical Co., Ltd., trade name "PSD-HP" produced by Nippon Soda Co., Ltd., trade name "Orange 100" produced by Yamada Chemical Co., Ltd., trade name "Leuco Yellow" produced by Leuco, trade name "Green 300" produced by Yamada Chemical Co., Ltd., trade name "YK-ATP" produced by Yamamoto Chemicals Inc., trade name "Green 300" produced by Hodogaya Chemical Co., Ltd., trade name "Blue 200" produced by Hodogaya Chemical Co., Ltd., trade name "CVL. sp" produced by Hodogaya Chemical Co., Ltd., trade name "5205" produced by Yamada Chemical Co., Ltd., and trade name "Black 100" produced by Yamada Chemical Co., Ltd.

5. A paper diaper according to claim 1, wherein the color development assisting agent contains at least one of polyphenol, catechin, tannin, gallnut, gallic acid, propyl gallate, persimmon tannin, green tea catechin (green tea tannin), green tea polyphenol, apple tannin, grape tannin, perilla tannin, perilla seed tannin, cacao tannin, cacao polyphenol, ascorbic acid, thiamine hydrochloride, adipic acid, citric acid, glycolic acid, succinic acid, tartaric acid, sebasic acid, sorbic acid, lactic acid, fumaric acid, and malic acid.

6. A paper diaper according to claim 1, wherein the indicator portion contains a surfactant.

7. A paper diaper according to claim 1, wherein the indicator portion covers the entirety of a part of the back sheet which is in contact with the absorption body.

8. A paper diaper according to claim 1, wherein the indicator portion is formed of at least one of a graphic pattern, a designed pattern, and a letter.

* * * * *